(12) United States Patent
Han et al.

(10) Patent No.: US 8,052,855 B2
(45) Date of Patent: Nov. 8, 2011

(54) CARBON NANOTUBE GAS SENSOR AND METHOD OF MANUFACTURING THE SAME

(75) Inventors: Jung-im Han, Yongin-si (KR); Soo-hyung Choi, Yongin-si (KR); Jeong-hee Lee, Yongin-si (KR); Soo-suk Lee, Yongin-si (KR); Jeong-na Heo, Yongin-si (KR)

(73) Assignee: Samsung Electronics Co., Ltd. (KR)

( * ) Notice: Subject to any disclaimer, the term of this patent is extended or adjusted under 35 U.S.C. 154(b) by 456 days.

(21) Appl. No.: 11/745,522

(22) Filed: May 8, 2007

(65) Prior Publication Data

US 2008/0142361 A1    Jun. 19, 2008

(30) Foreign Application Priority Data

May 11, 2006   (KR) ................... 10-2006-0042387
Sep. 19, 2006  (KR) ................... 10-2006-0090465

(51) Int. Cl.
*G01N 27/403* (2006.01)
*G01N 27/414* (2006.01)

(52) U.S. Cl. ........ 204/431; 204/400; 977/742; 977/743; 977/953; 977/957; 422/83; 422/94

(58) Field of Classification Search .......... 204/400–435; 205/775–794.5; 422/83–98; 73/23.2–31.07; 977/957, 953, 742–743
See application file for complete search history.

(56) References Cited

U.S. PATENT DOCUMENTS

| 6,424,397 | B1 * | 7/2002 | Kuo ............................ 349/139 |
| 6,811,457 | B2 * | 11/2004 | Cheng et al. .................... 445/24 |
| 7,391,225 | B1 * | 6/2008 | Lee et al. ...................... 324/698 |
| 2001/0003045 | A1 * | 6/2001 | Davis et al. ..................... 435/16 |
| 2004/0232426 | A1 * | 11/2004 | Graham et al. .................. 257/77 |
| 2005/0129858 | A1 * | 6/2005 | Jin et al. ..................... 427/372.2 |
| 2005/0218397 | A1 * | 10/2005 | Tran ............................ 257/14 |
| 2005/0230270 | A1 * | 10/2005 | Ren et al. .................... 205/777.5 |
| 2008/0113301 | A1 * | 5/2008 | Jung et al. ..................... 430/315 |

FOREIGN PATENT DOCUMENTS

DE            10118200 A1 * 10/2002

OTHER PUBLICATIONS

Machine translation of Luyken et al., DE10118200A1, 2002.*

* cited by examiner

*Primary Examiner* — Kaj K Olsen
*Assistant Examiner* — Susan Thai
(74) *Attorney, Agent, or Firm* — Cantor Colburn LLP

(57) ABSTRACT

A carbon nanotube ("CNT") gas sensor includes a substrate, an insulating layer formed on the substrate, electrodes formed on the insulating layer, and CNT barriers that protrude higher than the electrodes in spaces between the electrodes to form gas detecting spaces. A method of manufacturing the gas sensor includes forming an insulating layer on a substrate, forming an electrode pattern on the insulating layer, coating CNT paste having a thickness greater than a thickness of electrodes in the electrode pattern on the electrodes and the insulating layer, and patterning and firing the carbon nanotube paste, including using a photolithography method, to retain only portions of the CNT paste coated on spaces between the electrodes.

9 Claims, 5 Drawing Sheets

CARBON NANOTUBE GAS SENSOR AND METHOD OF MANUFACTURING THE SAME

This application claims priority to Korean Patent Application No. 10-2006-0042387 filed on May 11, 2006 and Korean Patent Application No. 10-2006-0090465 filed on Sep. 19, 2006, and all the benefits accruing therefrom under 35 U.S.C. §119, and the contents of which in their entireties are herein incorporated by reference.

BACKGROUND OF THE INVENTION

1. Field of the Invention

The present invention relates to a carbon nanotube ("CNT") gas sensor and a method of manufacturing the same, and more particularly, to a CNT gas sensor that has low operating temperature, low power consumption, and high sensitivity and a method of manufacturing the CNT gas sensor.

2. Description of the Related Art

Generally, a gas sensor measures the amount of a harmful gas using the characteristics of varying electrical conductivity or electrical resistance according to adsorption of gas molecules. Conventionally, a gas sensor was manufactured using a metal oxide semiconductor ("MOS"), a solid electrolyte material, or organic materials. However, the gas sensor that uses the MOS or the solid electrolyte material starts a sensing operation when the gas sensor is heated to 200-600° C. The gas sensor that uses the organic material has a very low electrical conductivity, and the gas sensor that uses carbon black and an organic complex has a very low sensitivity. In particular, when the gas sensor is manufactured using a complex of carbon black and an organic material, the gas sensor shows very low sensitivity.

Carbon nanotubes ("CNTs") have recently drawn attention as a new material that can be applied to various industrial fields due to their high electron emission characteristics and high chemical reactivity. In particular, the CNT is a material that has a very wide surface area compared to the volume of the CNT. Therefore, the CNT is very useful in fields such as hydrogen storing and the detection of a minor chemical component together with high surface reactivity. The advantages of the CNTS are derived from the properties of the CNTS. The CNTs, which are rolled carbon molecules formed by rolling graphite plates into cylinders (composed of $sp^2$ bonds) that consist of carbons connected by hexagonal rings, and have a diameter of a few to a few tens of nanometers nm. The CNTs are strong, flexible, and do not easily wear despite repeated use, and have different electrical characteristics according to the shape of their rolled up structure and diameter.

When the CNTs are used in a gas sensor, there are advantages in that a sensing operation can start at room temperature, and sensitivity and speed of response are very high since there is a large variation in electrical conductivity when harmful gases such as $NH_3$ or $NO_2$ react with the CNTs in the gas sensor.

There is a conventional gas sensor in which CNTs are grown between field effect transistor ("FET") type electrodes using a chemical vapor deposition ("CVD") method. At this time, the CNTs are grown using a solution in which CNT bundles are uniformly distributed in a solvent, for example, dimethylformamide, chloroform, dichloroethane, or methylpyrrolidinone.

However, the kinds of solvent in which the CNTs can be distributed are limited. Also, when the gas sensor is used for a long period of time, stability of the gas sensor is reduced due to low adhesiveness between the electrodes having a very fine structure and the CNTs. Furthermore, the reproducibility of the CNT sensor layer is difficult due to the characteristics of the CVD method. In particular, in the case of a gas sensor in which a few CNT elements having high sensitivity are connected, the manufacturing reproducibility can be very important. Also, since the CNTs are stacked to a very low height in a thin film state (in particular, when the CNTs are horizontally grown), a sensing space is formed to be very small and sensitivity is very low. Therefore, there is a difficulty in detecting a stable gas such as carbon dioxide.

BRIEF SUMMARY OF THE INVENTION

The present invention provides a carbon nanotube ("CNT") gas sensor that can improve adhesiveness between an electrode and CNTs, can increase yield by improving a stacking structure of the CNTs, and can rapidly detect in a short response time even a stable gas due to its high sensitivity.

According to exemplary embodiments of the present invention, a CNT gas sensor includes a substrate, an insulating layer formed on the substrate, electrodes formed on the insulating layer, and CNT barriers that protrude higher than the electrodes in spaces between the electrodes to form gas detecting spaces.

The CNT barriers may be formed of CNT paste coated on the insulating layer and the electrodes, and only portions of the CNT paste coated between the electrodes remain as the CNT barriers after patterning and firing the CNT paste using a photolithography method.

The CNT paste may include CNTs, a solvent, a binder that binds the CNTs and the electrodes, and a photoresist.

The binder may include an organic polymer, such as a methacrylate group organic polymer.

The photoresist may include an organic polymer that is cross-linked during exposing in the photolithography method.

The binder or the photoresist may include an organic polymer that is decomposed during firing.

The CNT barriers may have a resistance value of 100 kΩ or less after the CNT barriers are fired.

When the resistance between the electrodes before a gas reaction is called initial resistance, the resistance between the electrodes after a gas reaction is called final resistance, and sensitivity is defined as (final resistance−initial resistance)/initial resistance, the sensitivity may be 100% or more.

The electrodes may have an inter-digitated shape structure in which the electrodes are separated from each other.

The substrate may be formed of a transparent material, the electrodes may be formed of a non-transparent material, and light exposing the photoresist may be radiated from a rear of the substrate.

The CNT gas sensor may further include a heater layer that heats the CNT barriers to reduce the recovery time.

According to other exemplary embodiments of the present invention, a method of manufacturing a CNT gas sensor includes forming an insulating layer on a substrate, forming an electrode pattern on the insulating layer, coating CNT paste having a thickness greater than a thickness of electrodes in the electrode pattern on the electrodes and the insulating layer, and patterning and firing the carbon nanotube paste, including using a photolithography method, to retain only portions of the CNT paste coated on spaces between the electrodes.

BRIEF DESCRIPTION OF THE DRAWINGS

The above and other features and advantages of the present invention will become more apparent by describing in detail exemplary embodiments thereof with reference to the attached drawings in which.

DETAILED DESCRIPTION OF THE INVENTION

Figure 1:
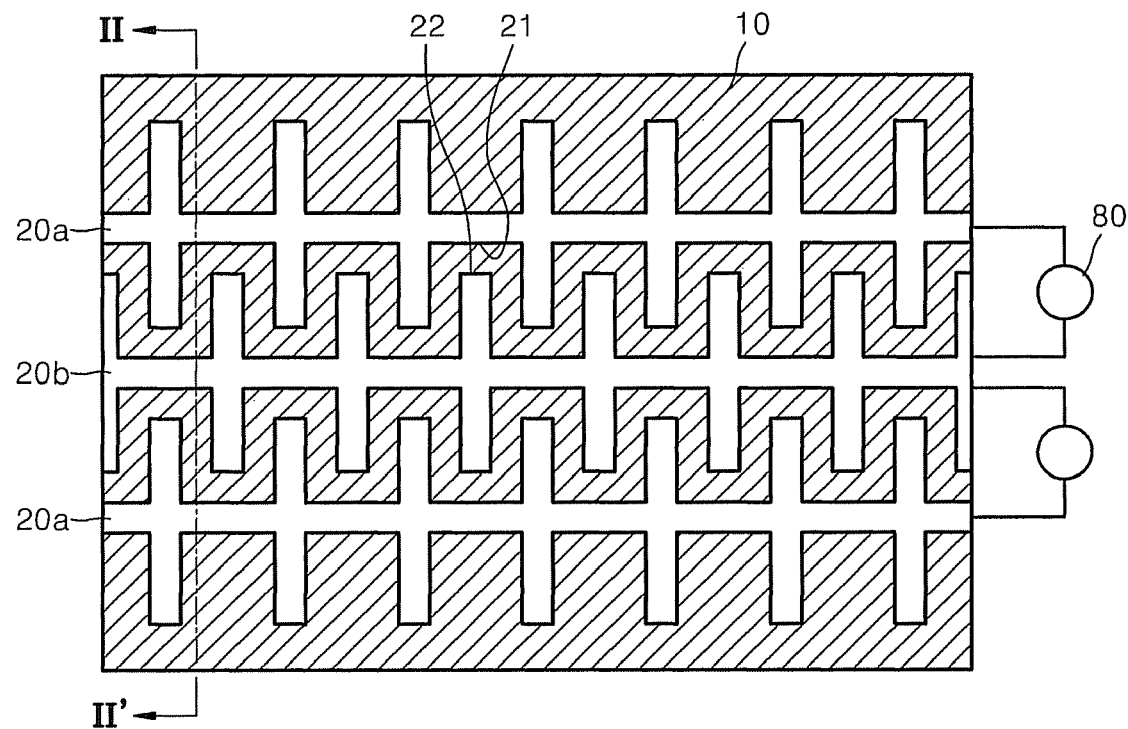
FIG. 1 is a top plan view illustrating a main portion of an exemplary CNT gas sensor according to an exemplary embodiment of the present invention.

The present invention will now be described more fully with reference to the accompanying drawings in which exemplary embodiments of the invention are shown. The embodiments of the present invention are not limited to the accompanied drawings but can be modified in various ways within the sprit of the present invention. These embodiments are provided so that this disclosure will be thorough and complete, and will fully convey the scope of the invention to those skilled in the art. Like reference numerals refer to like elements throughout.

It will be understood that when an element is referred to as being "on" another element, it can be directly on the other element or intervening elements may be present there between. In contrast, when an element is referred to as being "directly on" another element, there are no intervening elements present. As used herein, the term "and/or" includes any and all combinations of one or more of the associated listed items.

It will be understood that, although the terms first, second, third etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a first element, component, region, layer or section discussed below could be termed a second element, component, region, layer or section without departing from the teachings of the present invention.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Spatially relative terms, such as "beneath", "below", "lower", "above", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the exemplary term "below" can encompass both an orientation of above and below. The device may be otherwise oriented (rotated 90 degrees or at other orientations) and the spatially relative descriptors used herein interpreted accordingly.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Embodiments of the present invention are described herein with reference to cross section illustrations that are schematic illustrations of idealized embodiments of the present invention. As such, variations from the shapes of the illustrations as a result, for example, of manufacturing techniques and/or tolerances, are to be expected. Thus, embodiments of the present invention should not be construed as limited to the particular shapes of regions illustrated herein but are to include deviations in shapes that result, for example, from manufacturing. For example, a region illustrated or described as flat may, typically, have rough and/or nonlinear features. Moreover, sharp angles that are illustrated may be rounded. Thus, the regions illustrated in the figures are schematic in nature and their shapes are not intended to illustrate the precise shape of a region and are not intended to limit the scope of the present invention.

Hereinafter, the present invention will be described in detail with reference to the accompanying drawings.

Figure 2:
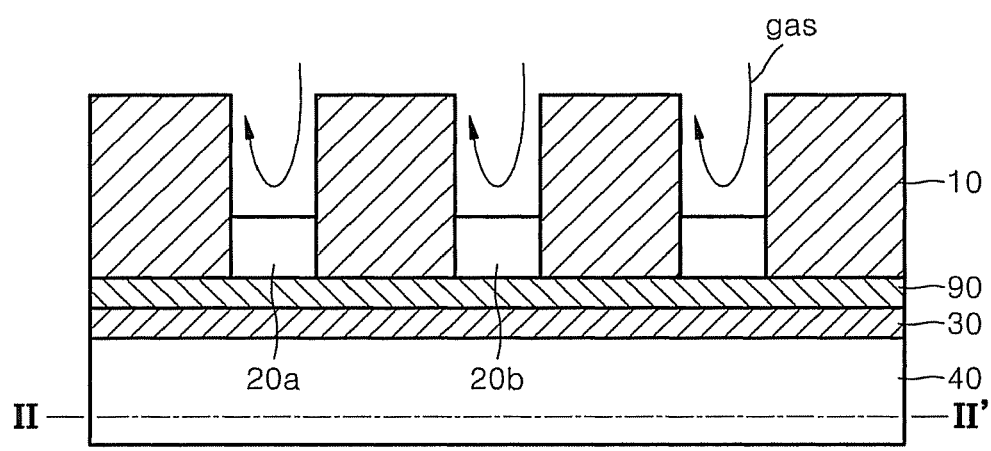
FIG. 2 is a cross-sectional view taken along line II-II' of FIG. 1.

FIG. 1 is a top plan view illustrating a main portion of an exemplary CNT gas sensor according to an exemplary embodiment of the present invention, and FIG. 2 is a cross-sectional view taken along line II-II' of FIG. 1. Referring to FIGS. 1 and 2, the main portion of the CNT gas sensor includes a substrate 40, an insulating layer 30, electrodes 20a and 20b, and CNT barriers 10. A heater 90 may also be included on the insulating layer 30, which will be further described below.

The insulating layer 30 is stacked on the substrate 40, and can be formed of various materials such as, but not limited to, silicon Si or silicon dioxide $SiO_2$. The electrodes 20a and 20b are formed on the insulating layer 30, are alternately disposed on the insulating layer 30, and can have various shapes. As illustrated, to increase contact area with a gas, the electrodes 20a and 20b may be formed in an inter-digitated shape in which the electrodes 20a and 20b are separated from each other. In such a case, the electrodes 20a and 20b respectively are formed by arranging concave parts 21 and convex parts 22 in series, and the concave parts 21 and the convex parts 22 of the electrodes 20a and 20b alternately face each other. Accordingly, empty spaces formed between the electrodes 20a and 20b, as locations for forming the CNT barriers 10, increase, thereby increasing contact surfaces with a gas. While a particular arrangement is described, other arrangements of the electrodes 20a and 20b are within the scope of these embodiments. The electrodes 20a and 20b can be formed of various materials, such as gold Au, titanium Ti, or an alloy of these metals.

The CNT barriers 10 are formed in the empty spaces between the electrodes 20a and 20b, and vertically protrude on the insulating layer 30 higher than the electrodes 20a and 20b to form gas detecting spaces there between. As depicted in FIG. 2, a gas circulates between the CNT barriers 10. The sensitivity and response time can be improved by increasing the height of the CNT barriers 10.

A gas adsorbed to the CNT barriers 10 changes electrical resistance of the CNT barriers 10. The amount of the gas is detected using the changes of electrical resistance or electrical conductivity. A gas detecting circuit 80 that detects a gas is connected to a pair of electrodes 20a and 20b. The gas detecting circuit 80 can be a voltage distribution circuit or a bridge circuit. If a voltage distribution circuit that measures voltage variation of CNTs is used as the gas detecting circuit 80, fine variation of resistance of the CNTs due to the adsorption of a gas can be detected in the form of voltage.

To ensure a correct operation of the gas sensor, the CNT barriers 10 must be formed to a certain thickness and height so that a predetermined number of the CNTs can be formed between the electrodes 20a and 20b, and adhesiveness of the CNTs with the electrodes 20a and 20b may be increased.

For this purpose, and as will be further described below with respect to exemplary methods of manufacturing exemplary carbon nanotube gas sensors, a CNT paste 11 (as shown, for example, in FIG. 3B) is coated on the entire surface, or substantially the entire surface, of the insulating layer 30 and the electrodes 20a and 20b. Afterwards, the CNT barriers 10 can be formed by patterning and firing the CNT paste 11, using a photolithography method, so that a portion of the CNT paste 11 coated in a space between the electrodes 20a and 20b can remain as the CNT barriers 10.

The CNT paste 11 having a predetermined viscosity can be made by mixing CNTs, a solvent such as α-terpineol, a methacrylate group organic polymer used as a binder between the CNTs and the electrodes 20a and 20b, and a photoresist, in a predetermined ratio. A sensitizer can further be included in the CNT paste 11.

In comparison to the CNT paste 11 having the above-described mixture, if a paste made by simply mixing a solvent and the CNTs is distributed on a substrate, then the selection of a solvent that can be mixed with the CNTs is very limited, the sensitivity of the resultant gas sensor can become a problem when the distribution of the CNTs is not uniform, and the stability of the resultant gas sensor can be reduced after being used for a period of time since no binder that increases adhesiveness with the electrodes 20a and 20b is included.

However, the CNT paste 11 according to exemplary embodiments of the present invention has improved adhesiveness with the electrodes 20a and 20b since a binder formed of an organic polymer is included in the CNT paste 11. The adhesiveness and the contact resistance of the CNTs with the electrodes 20a and 20b are improved by the decomposition of the binder formed of an organic polymer in a firing process, which will be described below. Here, the increase in the decomposition efficiency of the organic polymer during firing may be required.

Since the CNTs are coated in a paste state having a predetermined viscosity, the height of the CNT barriers 10 can be further increased, so as to have a greater height than a height of the electrodes 20a and 20b, and the number of CNTs present between a pair of the electrodes 20a and 20b can be maintained within a certain range.

The patterning of the CNT paste 11 is performed so that the CNT barriers 10 can be formed between the electrodes 20a and 20b. Therefore, the gas reaction area and porosity of the CNT barriers 10 increases, thereby increasing sensitivity of the gas sensor.

The exemplary CNT gas sensor according to the exemplary embodiments of the present invention, unlike the FET type conventional gas sensor, can be operated at room temperature, and has low power consumption as compared to a conventional gas sensor that detects a gas using the variation of surface potential when the gas is adsorbed since an additional heating element is unnecessary. The CNT gas sensor is a gas sensor that uses the characteristics of varying electrical conductivity or electrical resistance, and has a sensitivity 1000 times higher than that of a conventional gas sensor, but may have a long recovery time. In order to reduce the recovery time, the CNT gas sensor may further include a heater 90 that heats the CNT barriers 10 by limitedly operating during recovery time. The heater 90 may be disposed such that the insulating layer 30 is on one side of the heater 90 and the CNT barriers 10 and electrodes 20a, 20b are on an opposite side of the heater 90.

Figure 3A:
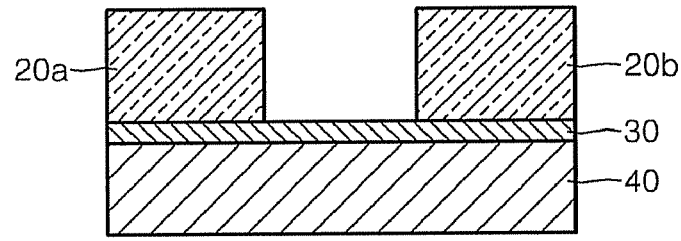
FIGS. 3A through 3C are lateral cross-sectional views illustrating a method of radiating light from a rear of a substrate in an exemplary method of manufacturing an exemplary CNT gas sensor according to an exemplary embodiment of the present invention.
Figure 3B:
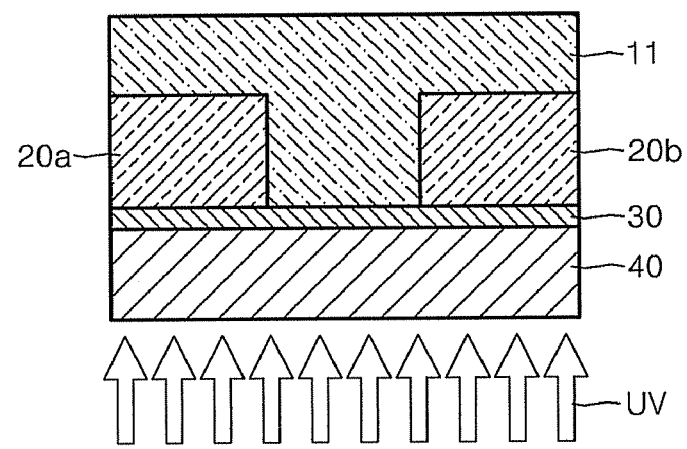
Figure 3C:
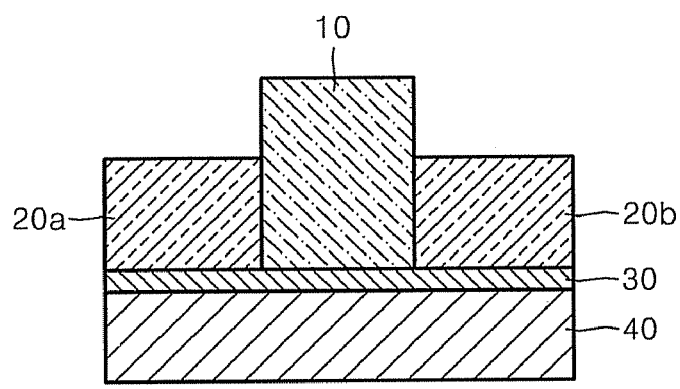

FIGS. 3A through 3C are lateral cross-sectional views illustrating a method of radiating light from a rear of a substrate 40 in an exemplary method of manufacturing an exemplary CNT gas sensor according to an exemplary embodiment of the present invention. The method of manufacturing a CNT gas sensor includes forming an insulating layer 30 on a substrate 40, forming patterns of electrodes 20a and 20b having inter-digitated shape structures separated from each other on the insulating layer 30, coating a CNT paste 11 having a thickness greater than the thickness of the electrodes 20a and 20b on the electrodes 20a and 20b and on the insulating layer 30, and firing only portions of the CNT paste 11 coated on spaces between the electrodes 20a and 20b using a photolithography method.

Referring to FIG. 3A, the insulating layer 30 is formed on the substrate 40 and the electrodes 20a and 20b are patterned on the insulating layer 30, such as to have the inter-digitated shape structures separated from each other as previously described with respect to FIGS. 1 and 2. In FIGS. 3B and 3C, a method of forming the CNT barriers 10 using a photolithography method is shown. The photolithography method is well known in the art, thus a detailed description thereof will be omitted.

Referring to FIG. 3B, the CNT paste 11 is coated to a thickness greater than the thickness of the electrodes 20a and 20b on the electrodes 20a and 20b and on the exposed portions of the insulating layer 30, and light (for example, ultraviolet "UV" rays) is radiated from the rear of the substrate 40 to expose a photoresist included in the CNT paste 11. That is, the light is radiated in the direction from the substrate 40 to the CNT paste 11. Here, the substrate 40 is formed of an optical transparent material, the electrodes 20a and 20b are formed of an optical shielding material, and the photoresist within the CNT paste 11 is a negative photoresist.

Referring to FIG. 3C, portions of the CNT paste 11 coated on the electrodes 20a and 20b are removed from the electrodes 20a and 20b by a developing agent since the portions of the CNT paste 11 coated on the electrodes 20a and 20b are not exposed due to the shielding effect of the electrodes 20a and 20b. The CNT paste 11, coated in a space between the electrodes 20a and 20b, remains on the substrate 30 since it is exposed through the optical transparent substrate 40. Therefore, the CNT barrier rib 10 between the electrodes 20a and 20b is formed to a height or thickness higher than or thicker than the height or thickness of the electrodes 20a and 20b by firing in a thermal treating process. The thermal treating process is a process of heating the resultant product to a firing temperature under $N_2$ or $O_2$ atmosphere, and at this time, the CNT barrier rib 10 has an electrical resistance of a measurable level, for example, a few to a few hundred kilohms kΩ. The adhesiveness of the CNT barrier rib 10 increases by the decomposition of the organic polymer included in the CNT paste 11 as a binder between the CNTs and the electrodes 20a and 20b. For example, the light is UV rays, and the photoresist in the CNT paste 11 is a UV photoresist.

Figure 4A:
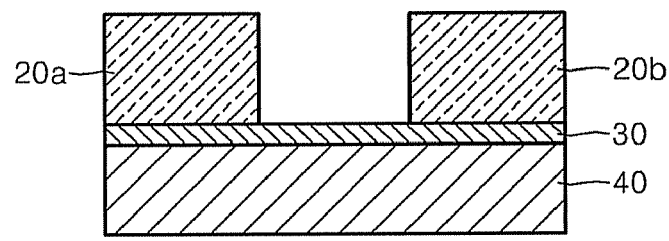
FIGS. 4A through 4C are lateral cross-sectional views illustrating a method of radiating light from above a substrate in which a negative photoresist is used in an exemplary method of manufacturing an exemplary CNT gas sensor according to an exemplary embodiment of the present invention.
Figure 4B:
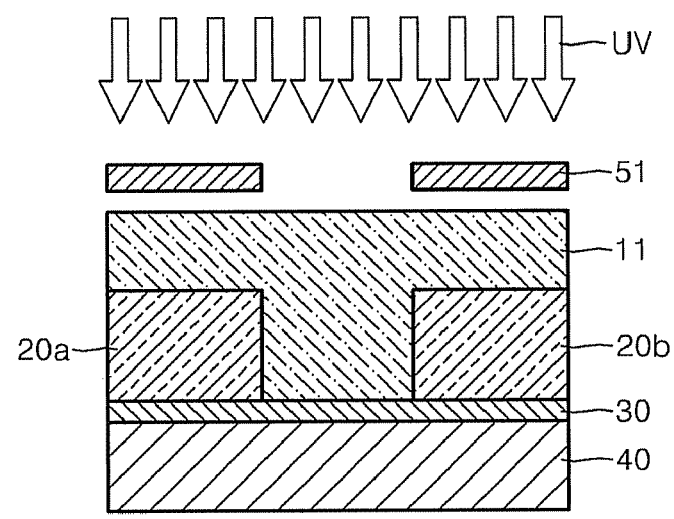
Figure 4C:
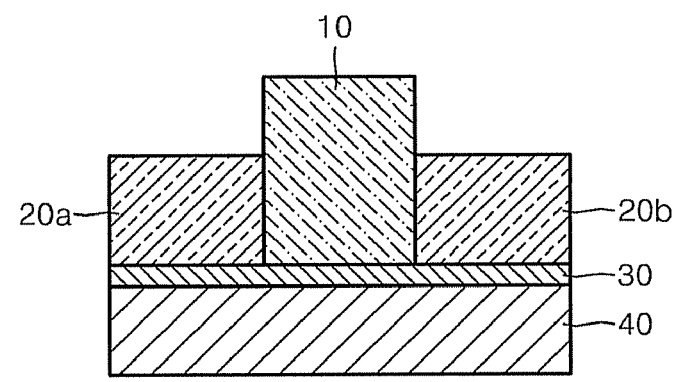

FIGS. 4A through 4C are lateral cross-sectional views illustrating a method of radiating light from above a substrate 40 in which a negative photoresist is used in an exemplary method of manufacturing an exemplary CNT gas sensor according to an exemplary embodiment of the present invention.

Referring to FIG. 4A, an insulating layer 30 and electrodes 20a and 20b are patterned as previously described with reference to FIG. 3A. In FIGS. 4B and 4C, a method of forming CNT barriers 10 using a photolithography method is shown.

Referring to FIG. 4B, the CNT paste 11 is coated to a thickness greater than the thickness of the electrodes 20a and 20b on the electrodes 20a and 20b and on the exposed portions of the insulating layer 30, and afterwards, light (for example, UV rays) is radiated from above the substrate 40 to expose a photoresist included in the CNT paste 11. That is, the light is radiated in a direction from the CNT paste 11 to the substrate 40. Here, the transparency of the substrate 40 and the electrodes 20a and 20b does not affect the radiation of light, the photoresist in the CNT paste 11 is a negative photoresist, and the portions of the CNT paste 11 coated on the electrodes 20a and 20b are shielded from the light by a mask 51, where the mask 51 includes openings aligned with the areas of the CNT paste 11 formed between the electrodes 20a and 20b, such that the light is radiated on such areas.

Referring to FIG. 4C, the portions of the CNT paste 11 coated on the electrodes 20a and 20b are removed by a developing agent due to being unexposed to the light, and the CNT paste 11 coated between the electrodes 20a and 20b remains on the substrate 30 since it is exposed. Therefore, the CNT barrier rib 10 between the electrodes 20a and 20b is formed to a higher height or greater thickness than the height or thickness of the electrodes 20a and 20b by firing in a thermal treating process.

Figure 5A:
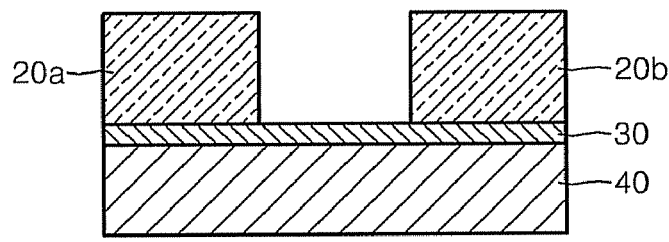
FIGS. 5A through 5C are lateral cross-sectional views illustrating a method of radiating light from above a substrate in which a positive photoresist is used in an exemplary method of manufacturing an exemplary CNT gas sensor according to an exemplary embodiment of the present invention.
Figure 5B:
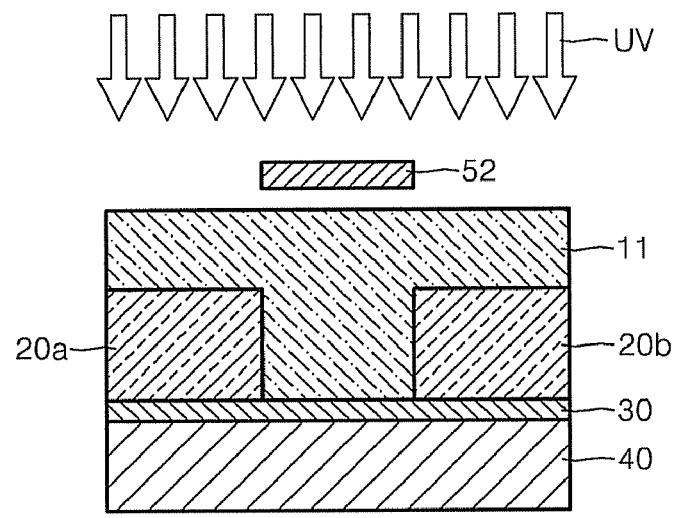
Figure 5C:
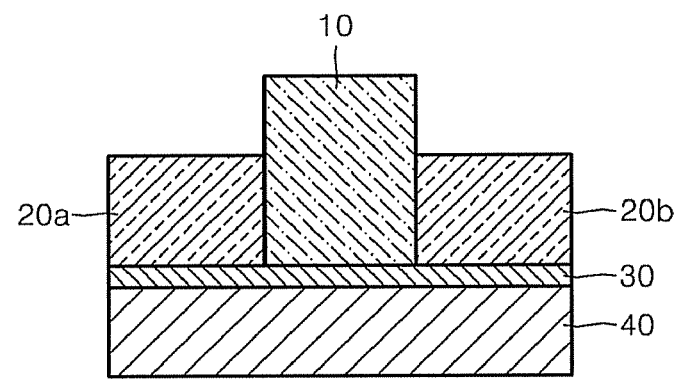

FIGS. 5A through 5C are lateral cross-sectional views illustrating a method of radiating light from above a substrate 40 in which a positive photoresist is used in an exemplary method of manufacturing an exemplary CNT gas sensor according to an exemplary embodiment of the present invention.

Referring to FIG. 5A, an insulating layer 30 and electrodes 20a and 20b are patterned as previously described with respect to FIG. 3A. In FIGS. 5B and 5C, a method of forming CNT barriers 10 using a photolithography method is shown.

Referring to FIG. 5B, the CNT paste 11 is coated to a thickness greater than the thickness of the electrodes 20a and 20b on the electrodes 20a and 20b and on the exposed portions of the insulating layer 30 between the electrodes 20a and 30b, and afterwards, light (for example, UV rays) is radiated from above the substrate 40 to expose a photoresist included in the CNT paste 11. That is, light is radiated in a direction from the CNT paste 11 to the substrate 40. Here, the transparency of the substrate 40 and the electrodes 20a and 20b does not affect the radiation of light, the photoresist in the CNT paste 11 is a positive photoresist, and the portion of the CNT paste 11 coated between the electrodes 20a and 20b is shielded from the light by a mask 52, where the mask 52 includes openings aligned with the areas of the CNT paste 11 formed on the electrodes 20a and 20b, such that the light is radiated on such areas.

Referring to FIG. 5C, the portions of the CNT paste 11 coated on the electrodes 20a and 20b are removed by a developing agent due to exposure to the light, and the CNT paste 11 coated between the electrodes 20a and 20b remains since it is unexposed to the light. Therefore, the CNT barrier rib 10 between the electrodes 20a and 20b is formed to higher height or greater thickness than the height or thickness of the electrodes 20a and 20b by firing in a thermal treating process.

Figure 6:
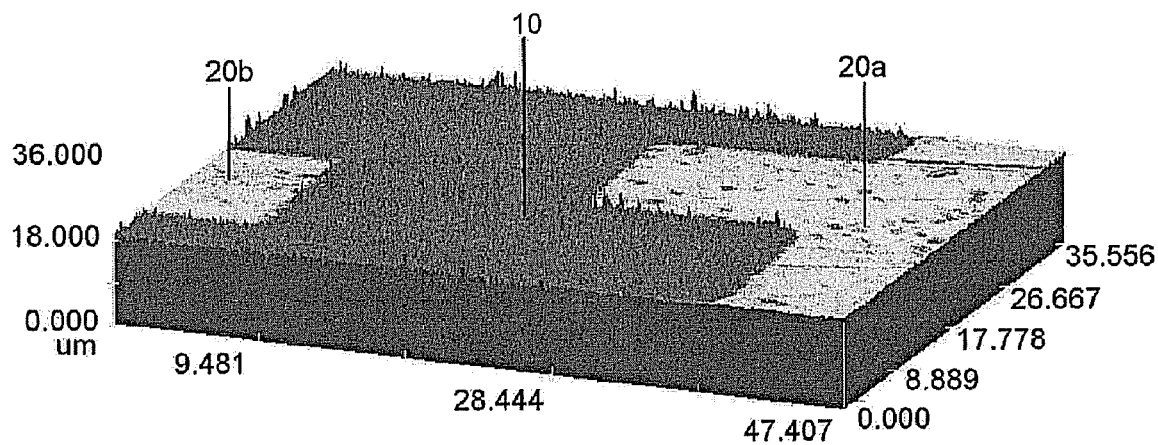
FIG. 6 is a scanning electron microscope ("SEM") image of a portion of an exemplary patterned CNT barrier rib between electrodes.

FIG. 6 is an SEM image of a portion of a CNT barrier rib 10 patterned between electrodes 20a and 20b. An experiment of patterning a CNT barrier rib 10 between electrodes 20a and 20b will now be described with reference to FIG. 6. A CNT paste was coated to a thickness greater than the thickness of an electrode on a substrate on which the electrode and an insulating layer are formed. The substrate on which the CNT paste was coated was dried by heating at a temperature of 60° C. for 30 minutes in a convection oven. As an exposure process, UV rays having a strength of 5 J/cm$^2$ and a wavelength of 405 nm were radiated. As a developing process, the CNT paste coated on portions to be removed were removed using a developing agent such as acetone. After impurities were removed using isopropylalcohol ("IPA") or ethanol ("EtOH"), the resultant product was washed using deionized water and dried. Afterwards, a temperature was increased to 430° C. at a rate of 5° C./min, and then the CNT barrier rib was fired for 20 minutes under an $N_2$ atmosphere.

For example, in the case of a CNT paste that does not include a photoresist, the resistance value of the CNT paste before firing was approximately 2.3Ω and after firing was approximately 2.3Ω. That is, there is practically no variation in the resistance value of the CNT paste between before and after firing and the resistance value itself is small, which are not desirable characteristics of a gas sensor.

However, in the case of the CNT paste that includes a photoresist or a sensitizer, the CNT barrier rib has a large value of resistance such as a few mega Ω or more (almost immeasurable large amount) before firing. This is because the photosensitizing material is a polymer having a large resistance. The polymer of the photosensitizing material included in the photoresist or the sensitizer is cross-linked by exposing. If there is no change in the cross-link state after firing, the photoresist or the sensitizer cannot be used for a gas sensor due to the large resistance value of the CNT paste. However, from the experiment, it is confirmed that the CNT barrier rib formed of the CNT paste in which a photoresist or a sensitizer is mixed has a resistance value of 100 KΩ or less due to the change in the cross-link state of the photosensitizing material after firing. This level of resistance value is similar to the resistance level of a thick film type (MOS type) gas sensor formed of a metal oxide. The low resistance value level was achieved by the decomposition of an organic polymer included in the binder, the photoresist, and the sensitizer as described above in a thermal treating process.

Here, in the conducted experiment, the gas sensor has dimensions of width×length=5 mm×5 mm; In FIG. 6, a portion of a gas sensor is shown. An electrode having a thickness of approximately 1000 Å, a width W of approximately 20 μm, and an electrode gap d of approximately 15 μm was used. A resistance (the initial resistance) between electrodes before a gas reaction was measured at room temperature, and a resistance (the final resistance) between electrodes after a reaction between the gas sensor and an $NH_3$ gas having a concentration of 100 ppm was measured. Here, it is defined that the sensitivity=(final resistance−initial resistance)/initial resistance.

For example, in the case of the $NH_3$ gas, the $NH_3$ gas is an electron donor since the $NH_3$ gas has a non-shared electron pair. When an electron is supplied to a common CNT, the CNT shows P-type semiconductor characteristics, that is, electrical conductance of the CNT is reduced and resistance of the CNT increases. Accordingly, when the $NH_3$ gas reacts with the CNT barrier rib 10, the final resistance increases greater than the initial resistance.

Table 1 summarizes the measurement results of initial resistance, final resistance, and sensitivity. Here, the first specimen represents a structure in which a CNT paste that does not include a photoresist was coated on a substrate. The second specimen represents a gas sensor in which, after a CNT paste that includes a photoresist was coated on the entire surface of a substrate, the substrate was fired but not patterned. The third specimen represents a gas sensor in which, after a CNT paste that includes a photoresist was coated on the entire surface of a substrate, the substrate was fired and patterned, that is, all processes were performed.

TABLE 1

| | Initial resistance kΩ | Final resistance kΩ | Sensitivity % |
|---|---|---|---|
| First specimen | 0.0023 | 0.0023 | 0 |
| Second specimen | 15.28 | 17.02 | 11.39 |
| Third specimen | 1.04 | 2.2 | 111.54 |

In the case of the first specimen, since the first specimen did not include a photoresist and a sensitizer, the gas sensor has very low initial and final resistances, has a characteristic close to a conductor, has no variation in resistance before and after reaction, and has sensitivity close to 0. Thus, such a construction cannot be used as a gas sensor.

In the case of the second specimen, since the second specimen was not exposed and patterned and was simply thermally treated, the photosensitizing material was not cross-linked. The measured resistance value lies within a measurable range but the sensitivity is only 11.39%.

In the case of the third specimen, the organic polymer was cross-linked by exposing in a patterning process in which the CNT barrier rib 10 is only formed on a portion between electrodes 20a and 20b, the organic polymer in the CNT paste was decomposed through the firing process, and the initial resistance value is lower than in the second specimen. Also, gas reactivity was improved due to the patterning, and thus, there is a large resistance variation between the initial resistance and the final resistance, thereby increasing sensitivity. The sensitivity of the third specimen is 111.54%, which is many times larger than the sensitivity of the second specimen.

Thus, a gas sensor according to the present invention has the following advantages.

First, in the gas sensor according to the present invention, a gas adsorption area and porosity are increased by patterned shapes of electrodes and CNT barriers. Thus, gas reactivity, gas permeability, and sensitivity of the gas sensor are increased, and response time and recovery time of the gas sensor can be reduced. If an additional heater is provided, the recovery time can further be reduced.

Second, the vertical growing of the CNT barriers to a predetermined height is simplified since the CNTs are coated in a paste state.

Third, since an organic polymer included in a binder or a photoresist is cross-linked and decomposed by exposing and firing, the electrical resistance of CNT barriers can be maintained within a measurable range, the sensitivity is greatly increased, and a predetermined adhesiveness and stability of the gas sensor are maintained even when the gas sensor is used for a period of time.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A carbon nanotube gas sensor comprising:
   a substrate;
   an insulating layer formed on the substrate;
   electrodes formed on a same plane of the insulating layer; and
   carbon nanotube barriers, which
      protrude higher than the electrodes, and
      are disposed in spaces between the electrodes; and
      gas detecting spaces formed on the electrodes between the carbon nanotube barriers; wherein ends of the carbon nanotube barriers are exposed, and the carbon nanotube barriers each comprise a plurality of carbon nanotubes, a first organic polymer, and a different second organic polymer.

2. The carbon nanotube gas sensor of claim 1, wherein the carbon nanotube barriers have an initial resistance value of 100 kΩ or less, wherein the initial resistance is a resistance between the electrodes before a gas reaction.

3. The carbon nanotube gas sensor of claim 2, wherein sensitivity, defined as (final resistance−initial resistance)/initial resistance, is 100% or more, where the final resistance is a resistance between the electrodes after a gas reaction.

4. The carbon nanotube gas sensor of claim 1, wherein
   the substrate is formed of a transparent material, and
   the electrodes are formed of a non-transparent material.

5. The carbon nanotube gas sensor of claim 1, wherein electrodes have an inter-digitated shape structure in which the electrodes are separated from each other.

6. The carbon nanotube gas sensor of claim 1, further comprising a heater layer that heats the carbon nanotube barriers to reduce a recovery time.

7. The carbon nanotube gas sensor of claim 1, wherein the first organic polymer binds the carbon nanotubes and the electrodes, and the second organic polymer increases a sensitivity of the carbon nanotube barriers.

8. The carbon nanotube gas sensor of claim 5, wherein the electrodes have at least one first electrode and at least one second electrode which have a plurality of concave parts and convex parts, respectively.

9. The carbon nanotube gas sensor of claim 8, wherein the concave parts and the convex parts of the first electrode and the second electrode alternately face each other.

* * * * *